United States Patent [19]
Endoh et al.

[11] Patent Number: 6,022,997
[45] Date of Patent: Feb. 8, 2000

[54] PROCESS FOR PREPARING TRIPHENYLAMINE COMPOUNDS BY USING A NITROGEN TRIHALIDE

[75] Inventors: Hiroyuki Endoh; Tsutomu Uezono, both of Tokyo, Japan

[73] Assignee: NEC Corporation, Tokyo, Japan

[21] Appl. No.: 09/280,981

[22] Filed: Mar. 30, 1999

[30] Foreign Application Priority Data

Mar. 30, 1998 [JP] Japan .................................. 10-084106
Feb. 5, 1999 [JP] Japan .................................. 11-029093

[51] Int. Cl.$^7$ ................................................. C07C 209/00
[52] U.S. Cl. ............................................................ 564/412
[58] Field of Search ............................................... 564/412

[56] References Cited

U.S. PATENT DOCUMENTS

| | | | |
|---|---|---|---|
| 3,820,989 | 6/1974 | Rule et al. .................................. | 96/1.5 |
| 4,769,302 | 9/1988 | Ueda ......................................... | 430/59 |
| 5,733,697 | 3/1998 | Endoh et al. .............................. | 430/59 |

FOREIGN PATENT DOCUMENTS

| | | |
|---|---|---|
| 58-65440 | 4/1983 | Japan . |
| 62-120346 | 6/1987 | Japan . |
| 63-19867 | 4/1988 | Japan . |
| 63-163361 | 7/1988 | Japan . |
| 5-42661 | 6/1993 | Japan . |
| 6-93124 | 11/1994 | Japan . |
| 7-13741 | 2/1995 | Japan . |
| 9-292724 | 11/1997 | Japan . |

OTHER PUBLICATIONS

Kovacic, P., et al., "Chemistry of N–Halamines: Amination of Alkyl Halides with Trichloramine–Aluminum Chloride," J. Org. Chem., vol. 34, No. 4, pp. 911–917 (1969).

Primary Examiner—Paul J. Killos
Attorney, Agent, or Firm—Foley & Lardner

[57] ABSTRACT

This invention provides a process for the preparation of triphenylamine compounds useful as charge transport materials. According to this process, a triphenylamine compound of the general formula (2)

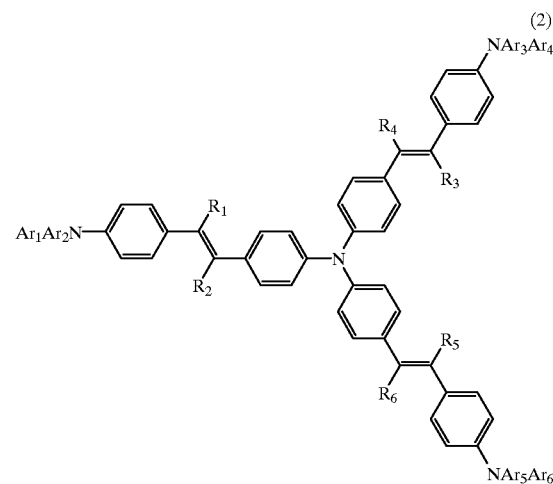

of the general formula (1)

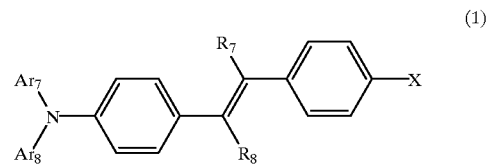

into a lithio compound, and reacting the lithio compound with a nitrogen trihalide. In the above formulae, $Ar_1$ to $Ar_8$ each represent an optionally substituted phenyl radical, $R_1$ to $R_8$ each represent a hydrogen atom or a methyl group, and X represents a halogen atom.

8 Claims, No Drawings

PROCESS FOR PREPARING TRIPHENYLAMINE COMPOUNDS BY USING A NITROGEN TRIHALIDE

BACKGROUND OF THE INVENTION

1. Field of the Invention

This invention relates to a process for the preparation of triphenylamine compounds. More particularly, it relates to a process for the preparation of triphenylamine compounds which are useful as charge transport materials (or hole transport materials) contained in electrophotographic sensitive materials.

2. Description of the Prior Art

Conventionally, inorganic photoconductors such as selenium (Se), cadmium sulfide (CdS), zinc sulfide (ZnS) and amorphous silicon (a-Si) have been known to be useful in photosensitive materials for use in electrophotography. Although these inorganic photosensitive materials have many advantages, they also have various disadvantages, for example, in that they are harmful, they cannot be easily disposed of, and they are expensive. For this reason, a variety of organic photosensitive materials using organic substances free of such disadvantages have recently proposed and put to practical use. From the viewpoint of structure, such photosensitive materials include separated-function type photosensitive materials in which a material for generating charge carriers (hereinafter referred to as the "charge-generating material") and a material for accepting the generated charge carriers and transporting them (hereinafter referred to as the "charge transport material") are formed into separate layers, and single-layer type photosensitive materials in which charge generation and charge transport are effect in the same layer. However, separated-function type photosensitive materials are more commonly used because they have a wide choice of materials and they can be designed to have high sensitivity.

As the charge transport medium, there may be used either a polymeric photoconductive compound such as polyvinyl carbazole, or a low-molecular-weight photoconductive compound dispersed or dissolved in a binder polymer. Polymeric photoconductive compounds, when used alone, have insufficient film-forming properties and bonding properties. In order to improve these properties, a plasticizer, a binder polymer and the like are added thereto. However, these additives may cause a reduction in sensitivity and an increase in residual potential, so that the resulting products cannot be easily used for practical purposes. On the other hand, low-molecular-weight photoconductive compounds can readily yield photosensitive materials having excellent mechanical properties by selecting a suitable binder polymer, but cannot be said to have sufficiently high sensitivity. For example, the diarylalkane derivatives described in U.S. Pat. No. 3,820,989 have no appreciable problem from the viewpoint of compatibility with binder polymers, but their stability to light is poor. Accordingly, these compound have the disadvantage that, when they are used in the photosensitive layer of a electrophotographic sensitive material which is repeatedly charged and exposed to light, the sensitivity of this material is gradually reduced during repeated use. Moreover, the stilbene compounds described in Japanese Patent Laid-Open No. 65440/'83 have relatively high charge-holding capacity and sensitivity, but fail to exhibit satisfactory stability during repeated use.

The monostyryltriphenylamine compounds [for example, of formula (101)] described in Japanese Patent Publication No. 019867/'88, the distyryltriphenylamine compounds [for example, of formula (102)] described in Japanese Patent Publication No. 042661/'93 and Japanese Patent Laid-Open No. 120346/'87, and the tristyryltriphenylamine compounds [for example, of formula (103)] described in Japanese Patent Publication No. 093124/'94 and Japanese Patent Laid-Open No. 163361/'88 have high charge-holding capacity and sensitivity, and exhibit good stability during repeated use. However, they fail to give sufficient charge mobility, and are hence unsatisfactory as charge transport materials for use in high-speed electrophotographic sensitive materials. In these compounds as represented by formulae (101) to (103), only one triphenylamine structure [of formula (201)] serving as a hopping site for charges is contained in the molecule. Consequently, they fail to give sufficient charge mobility and, therefore, cannot exhibit sufficient sensitivity. Although various substituents may be introduced into these compounds, it has not been described therein to introduce a plurality of triphenylamine structures. Moreover, an electrophotographic sensitive material using a mixture of two or more of the aforesaid triphenylamine compounds is described in Japanese Patent Publication No. 013741/'95, but each compound contains only one triphenylamine structure. Thus, no compound containing a plurality of triphenylamine structures is described therein.

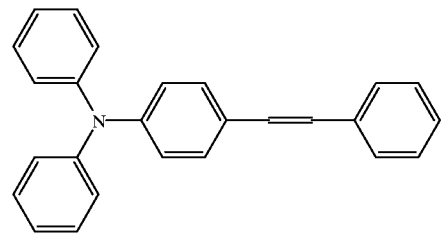

(101)

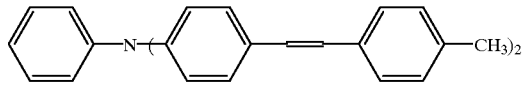

(102)

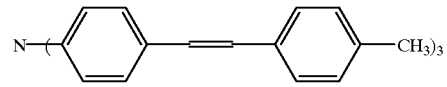

(103)

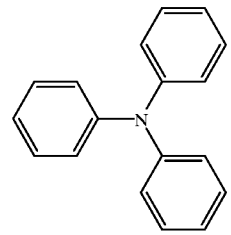

(201)

The triphenylamine compounds [of the following formula (2)] described in Japanese Patent Application No. 002844/'97 can satisfy the above-described requirements.

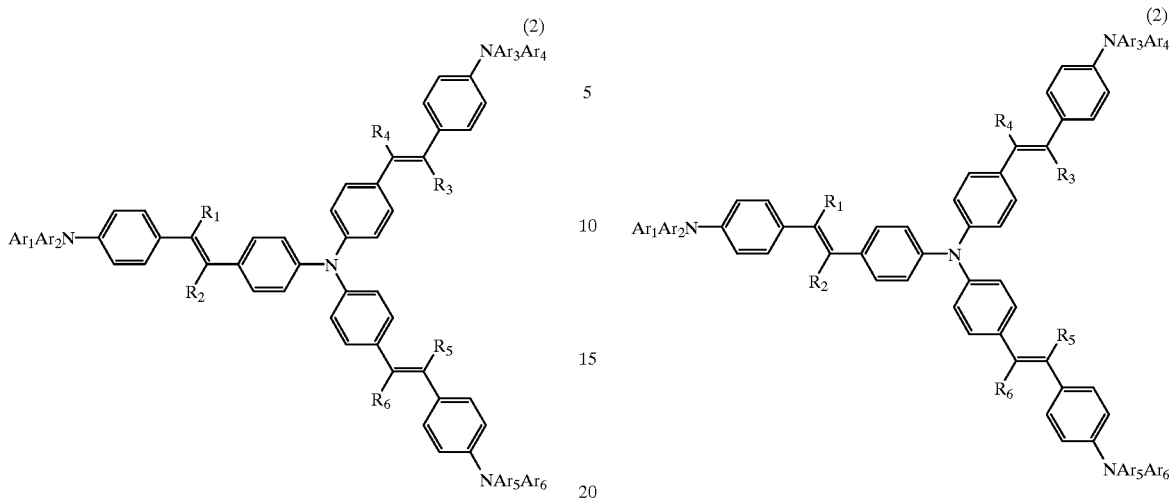

wherein $Ar_1$ to $Ar_6$ each represent an unsubstituted phenyl radical or a substituted phenyl radical having one or more substituents on the phenyl nucleus in which the substituents may be the same or different and each comprise an alkyl group of 1 to 4 carbon atoms, an alkoxy group of 1 to 4 carbon atoms, an amino group, an alkylamino group of 1 to 4 carbon atoms, a dialkcylamino group of 1 to 4 carbon atoms, an alkylthio group of 1 to 4 carbon atoms, a halogen atom, or a halogenoalkyl group of 1 to 4 carbon atoms, and $R_1$ to $R_6$ may be the same or different and each represent a hydrogen atom or a methyl group.

The triphenylamine compounds of formula (2) can be prepared by the Wittig reaction for condensing a tricarbonyl compound such as 4,4',4"-triformyltriphenylamine or 4,4',4"-triacetyltriphenylamine with a phosphonic ester in the presence of a base. However, difficulty is frequently encountered in introducing a plurality of carbonyl groups into a compound, so that it has been difficult to synthesize the desired triformyl compound efficiently. Moreover, phosphorous esters of amino compounds are generally unstable, so that it has been difficult to prepare the desired compound efficiently.

SUMMARY OF THE INVENTION

An object of the present invention is provide a process which permits triphenylamine compounds of the above formula (2) to be prepared efficiently.

According to the present invention, there is provided a process for the preparation of a triphenylamine compound of the general formula (2)

wherein $Ar_1$ to $Ar_6$ each represent an unsubstituted phenyl radical or a substituted phenyl radical having one or more substituents on the phenyl nucleus in which the substituents may be the same or different and each comprise an alkyl group of 1 to 4 carbon atoms, an alkoxy group of 1 to 4 carbon atoms, an amino group, an alkylamino group of 1 to 4 carbon atoms, a dialkylamino group of 1 to 4 carbon atoms, an alkylthio group of 1 to 4 carbon atoms, a halogen atom, or a halogenoalkyl group of 1 to 4 carbon atoms, and $R_1$ to $R_6$ may be the same or different and each represent a hydrogen atom or a methyl group, said process comprising the steps of converting at least one halogen compound of the general formula (1)

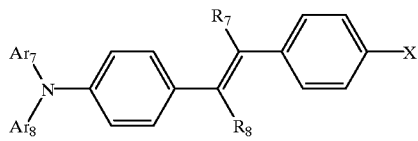

wherein $R_7$ and $R_8$ may be the same or different and each represent a hydrogen atom or a methyl group, $Ar_7$ and $Ar_8$ may be the same or different and each represent an unsubstituted phenyl radical or a substituted phenyl radical having one or more substituents on the phenyl nucleus in which the substituents may be the same or different and each comprise an alkyl group of 1 to 4 carbon atoms, an alkoxy group of 1 to 4 carbon atoms, an amino group, an alkylamino group of 1 to 4 carbon atoms, a dialkylamino group of 1 to 4 carbon atoms, an alkylthio group of 1 to 4 carbon atoms, a halogen atom, or a halogenoalkyl group of 1 to 4 carbon atoms, and X represents a halogen atom, into a lithio compound, and reacting the lithio compound with a nitrogen trihalide in which the three halogen atoms joined to the nitrogen atom may be the same or different.

DETAILED DESCRIPTION OF THE INVENTION

According to the process of the present invention, it is unnecessary to introduce a plurality of carbonyl groups into triphenylamine. Moreover, it is also unnecessary to form a phosphorous ester of an amino compound as an intermediate product. Consequently, the compound of formula (2) [the compound of formula (2) or the like may hereinafter be referred to briefly as the compound (2) or the like] can be prepared more efficiently than when the conventional process is employed.

The compound (1) may be prepared by reacting a 4-halogenobenzyl halide of formula (3) or a 1-halogeno-4-(1-halogenoethyl)benzene of formula (4) with triethyl phosphite, and reacting the resulting phosphorous ester [of formula (5) or (6)] with a diphenylaminobenzaldehyde of formula (7).

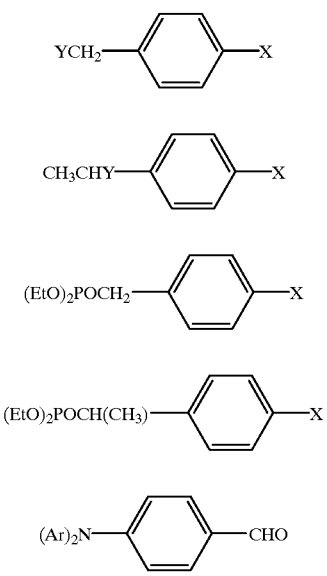

In the compounds (3) and (4), the substituent X comprises a halogen atom and preferably a chlorine, bromine or iodine atom. The substituent X also comprises a halogen atom. The substituents X and Y may be the same or different.

The reaction of the phosphorous ester (5) or (6) with the diphenylaminobenzaldehyde (7) is carried out in a suitable solvent, at room temperature or under heated conditions, and in the presence of a basic catalyst. The bases which can be used for this purpose include alcoholates (e.g., sodium methylate, sodium ethylate and potassium t-butylate), sodium hydroxide, potassium hydroxide, sodium amide and sodium hydride.

The solvents which can be used for this purpose include aromatic hydrocarbons such as toluene and benzene; alcohols such as methanol, ethanol and isopropyl alcohol; ethers such as dioxane and tetrahydrofuran; N,N-dimethylformamide; and dimethyl sulfoxide. Especially preferred are toluene and N,N-dimethylformamide. No particular limitation is placed on the amount of solvent used, and it is suitable to use the solvent in an amount of 1 to 10 parts by weight per part by weight of the reactants. The reaction is carried out at a temperature ranging from room temperature to 100° C. and preferably from 20 to 70° C. After completion of the reaction, the product is isolated by filtration or extraction. If necessary, the product is purified according to a well-known method such as recrystallization, column chromatography or distillation.

The conversion of the compound (1) into a lithio compound is carried out by reacting the compound (1) with a lithio-forming agent such as methyllithium or butyllithium.

Subsequently, the resulting lithio compound is reacted with a nitrogen trihalide to eliminate a lithium halide. Thus, the desired compound (2) is obtained.

The nitrogen trihalides which can be used for this purpose include nitrogen trichloride ($NCl_3$), nitrogen trifluoride ($NF_3$) and nitrogen tribromide ($NBr_3$). Moreover, compounds having different halogen atoms joined to the nitrogen atom, such as nitrogen monofluoride dichloride ($NCl_2F$), nitrogen difluoride monochloride ($NClF_2$), nitrogen monochloride dibromide ($NBr_2Cl$) and nitrogen dichloride monobromide ($NBrCl_2$) may also be used for this reaction.

For this purpose, the nitrogen trihalide gas which is commonly used in the semiconductor industry may be used as such. Alternatively, this gas may be used in the form of a solution prepared by dissolving it in an organic solvent.

Nitrogen trichloride can be obtained according to the method described by P. Kovaic et al. in J. Org. Chem., Vol. 34, p. 911 (1969).

Nitrogen tribromide may be prepared from nitrogen trichloride and an aqueous solution of potassium bromide.

As the reaction solvent, there may be used any of various solvents including chlorine-containing solvents such as methylene chloride and chloroform; aromatic hydrocarbon solvents such as benzene and toluene; and ether solvents such as diethyl ether and tetrahydrofuran. Although the reaction temperature may vary widely from a very low temperature to the boiling point of the solvent, it is preferable to carry out the reaction at a temperature of −20 to 0° C. If necessary, a Lewis acid such as aluminum chloride may be used as the reaction catalyst.

EXAMPLES

The present invention is further illustrated by the following examples. However, these examples are not to be construed to limit the scope of the invention.

Example 1

(1) Preparation of a Phosphorous Ester

A 200 ml eggplant type flask fitted with a reflux condenser was mounted on a magnetic stirrer. 20 g (124 mmol) of 4-chlorobenzyl chloride was placed in the flask, and 25 g (150 mmol) of triethyl phosphite was added thereto. While this mixture was stirred with the magnetic stirrer, the flask was heated in an oil bath. Thus, the mixture was refluxed with stirring for 8 hours. After completion of the reaction, unreacted triethyl phosphite was distilled off by evacuating the flask with a pump. As the residue remaining in the flask, 30.9 g of a phosphorous ester was obtained in a 95% yield.

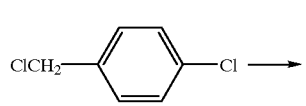

(2) Preparation of a Chlorine Compound

A 200 ml three-neck flask fitted with a drying tube and a dropping funnel was charged with 0.5 g (20 mmol) of sodium hydride and 50 ml of N,N-dimethylformamide to form a suspension, followed by stirring with a magnetic stirrer. Then, 5.0 g (19 mmol) of the above phosphorous ester was added to the flask, followed by stirring at room temperature for 1 hour. A solution prepared by dissolving 5.7 g (19 mmol) of 4-(4',4"-dimethyldiphenylamino) benzaldehyde in 15 ml of N,N-dimethylformamide was added through the dropping funnel and reacted at 40° C. for 10 hours. After completion of the reaction, water was added to the reaction mixture and the resulting mixture was extracted three times with toluene. The organic solution thus obtained was washed with a saturated aqueous solution of sodium chloride until the aqueous layer became neutral, and dried with magnesium sulfate.

After the magnesium sulfate was removed by filtration, the toluene solvent was distilled off under reduced pressure. The residue was recrystallized from a 7:3 mixture of toluene and ligroine to obtain 6.6 g of 4-chloro-4'-(N,N-ditolylamino)stilbene in an 85% yield.

obtained was washed with a saturated aqueous solution of sodium chloride, and dried with magnesium sulfate.

After the magnesium sulfate was removed by filtration, the product was isolated by silica gel chromatography using the toluene solvent. Moreover, the product was recrystallized from a 7:3 mixture of toluene and ligroine to obtain 1.4 g of 4,4',4"-tris[4-(N,N-ditolylamino)styryl]triphenylamine as a yellow powder in a 65% yield.

$^1$H-NMR, d(CDCl$_3$, ppm): 2.3(18H, s, CH$_3$x6), 6.8(3H, d, CHx3), 7.1(3H, d, CHx3), 7.0–8.0(48H, m, ArH).

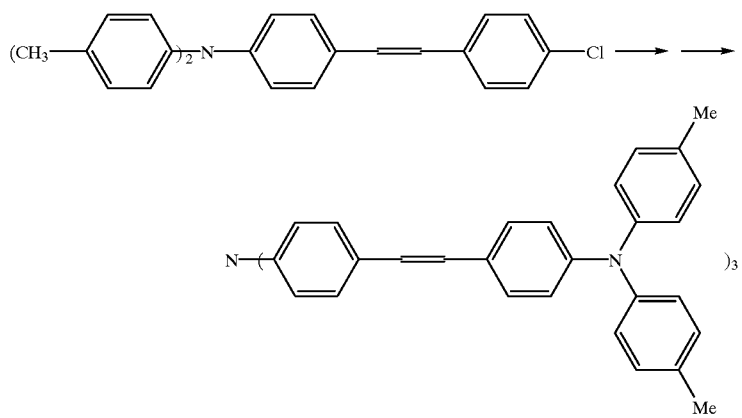

(10)

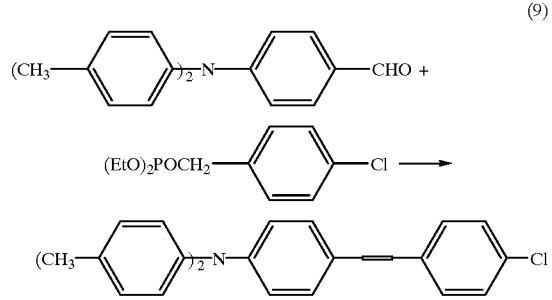

(9)

(3) Preparation of a Triphenylamine

A 100 ml three-neck flask fitted with a dropping funnel and a drying tube was charged with 2.0 g (4.9 mmol) of the above 4-chloro-4'-(N,N-ditolylamino)stilbene and 20 ml of tetrahydrofuran, followed by stirring. After the flask was cooled to −78° C., 1 ml of a solution of butyllithium in hexane (at a concentration of 1.6 mol/l) was added dropwise thereto through the dropping funnel. While the reaction temperature was kept at −78° C., the reaction mixture was stirred for an additional hour, and the temperature was allowed to rise to −20° C. Then, 4 ml of a toluene solution containing 0.19 g of nitrogen trichloride was slowly added dropwise thereto through the dropping funnel. After completion of the addition, the reaction mixture was stirred for an additional two hours. After completion of the reaction, the temperature was returned to room temperature, water was added to the reaction mixture, and the resulting mixture was extracted three times with toluene. The organic solution thus (4) An Electrophotographic Sensitive Material Using the Above Triphenylamine An undercoat layer (0.1 μm thick) comprising a methoxymethylated nylon (T-8; manufactured by Unitilka, Ltd.) was formed on an aluminum substrate, and a charge-generating layer (0.1 μm thick) containing n-type titanylphthalocyanine and polyvinyl butyral (BX-1; manufactured by Sekisui Chemical Co., Ltd.) was formed on the undercoat layer. Moreover, a 20 μm thick charge transport layer was formed thereon by applying a dichloroethane solution containing the 4,4',4"-tris[4-(N,N-ditolylamino) styryl]triphenylamine obtained in the above-described step (3) and a polycarbonate (Eupilon Z-200; manufactured by Mitsubishi Gas Chemical Co., Inc.) in a weight ration of 0.8:1. This solution exhibited good spreadability and yielded a coating film having a sufficient strength. The electrophotographic characteristics of the electrophotographic sensitive material so formed were evaluated by means of an electrostatographic testing apparatus (EPA 8100; manufactured by Kawaguchi Electric Works Co., Ltd.). Specifically, it was electrically charged by a corona discharge occurring at −6 kV, attenuated in the dark for 3 seconds, and exposed to white light having an intensity of 5 lux for 5 seconds. Thus, the time (in seconds) required to reduce its surface potential to ½ was measured to determine the half-value light exposure. Moreover, the residual surface potential after exposure to white light for 5 seconds was measured. As a result, its initial half-value light exposure was 0.238 lux·sec and its residual surface potential was −3 volts, indicating its excellent photosensitivity. After 1,000 test cycles, its initial half-value light exposure was 0.241 lux·sec and its residual surface potential was −5 volts. Thus, these measured values were similar to the initial values, indicating its excellent stability during repeated use.

Example 2

A 100 ml three-neck flask fitted with a dropping funnel, a drying tube and a gas inlet tube was charged with 2.0 g (4.9 mmol) of 4-chloro-4'-(N,N-itolylamino)stilbene, which had been prepared in the same manner as described in Example 1, and 20 ml of tetrahydrofuran, followed by stirring. After the flask was cooled to −78° C., 1 ml of a solution of butyllithium in hexane (at a concentration of 1.6 mol/l) was added dropwise thereto through the dropping funnel. While the reaction temperature was kept at −78° C., the reaction mixture was stirred for an additional hour, and the temperature was allowed to rise to −20° C. Then, 0.11 g of nitrogen trifluoride was introduced through the gas inlet tube. After introduction of the gas, the reaction mixture was stirred for an additional two hours. After completion of the reaction, the temperature was returned to room temperature, water was added to the reaction mixture, and the resulting mixture was extracted three times with toluene. The organic solution thus obtained was washed with a saturated aqueous solution of sodium chloride, and dried with magnesium sulfate.

After the magnesium sulfate was removed by filtration, the product was isolated by silica gel chromatography using the toluene solvent. Moreover, the product was recrystallized from a 7:3 mixture of toluene and ligroine to obtain 0.5 g of 4,4',4"-tris[4-(N,N-ditolylamino)styryl]triphenylamine as a yellow powder in a 23% yield.

Example 3

A 100 ml three-neck flask fitted with a dropping funnel and a drying tube was charged with 2.0 g (4.9 mmol) of 4-chloro-4'-(N,N-ditolylamino)stilbene, which had been prepared in the same manner as described in Example 1, and 20 ml of tetrahydrofuran, followed by stirring. After the flask was cooled to −78° C., 1 ml of a solution of butyllithium in hexane (at a concentration of 1.6 mol/l) was added dropwise thereto through the dropping funnel. While the reaction temperature was kept at −78° C., the reaction mixture was stirred for an additional hour, and the temperature was allowed to rise to −20° C. Then, 10 ml of a toluene solution containing 0.4 g of nitrogen tribromide was slowly added dropwise thereto through the dropping funnel. After completion of the addition, the reaction mixture was stirred for an additional two hours. After completion of the reaction, the temperature was returned to room temperature, water was added to the reaction mixture, and the resulting mixture was extracted three times with toluene. The organic solution thus obtained was washed with a saturated aqueous solution of sodium chloride, and dried with magnesium sulfate.

After the magnesium sulfate was removed by filtration, the product was isolated by silica gel chromatography using the toluene solvent. Moreover, the product was recrystallized from a 7:3 mixture of toluene and ligroine to obtain 1.1 g of 4,4',4"-tris[4-(N,N-ditolylamino)styryl]triphenylamine as a yellow powder in a 50% yield.

Example 4

Reaction was carried out in the same manner as described in Example 1 (1), except that 30 g (124 mmol) was used in place of 4-chlorobenzyl chloride. Thus, 37.3 g of a phosphorous ester was obtained in a 98% yield. This phosphorous ester was reacted in the same manner as described in Example 1 (2) to obtain an 81% yield of 4-bromo-4'-(N,N-ditolylamino)stilbene.

Using 2.2 g (4.9 mmol) of the above 4-bromo-4'-(N,N-ditolylamino)stilbene, reaction was carried out in the same manner as described in Example 1 (3) to obtain 1.2 g of 4,4',4"-tris[4-(N,N-ditolylamino)styryl]triphenylamine in a 62% yield.

As is evident from the above detailed description, triphenylamine compounds useful as hole transport materials can be efficiently produced according to the process of the present invention.

What is claimed is:
1. A process for the preparation of a triphenylamine compound of the general formula (2)

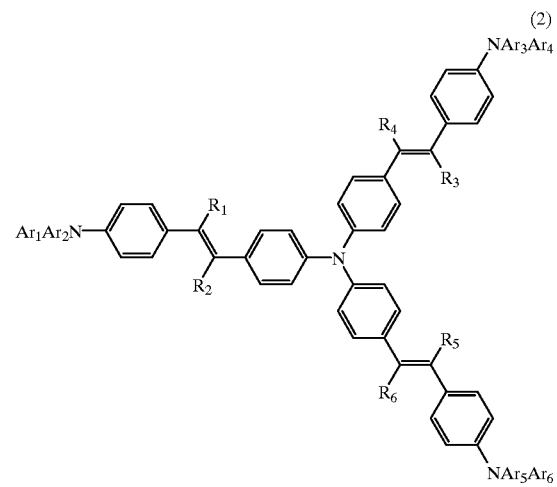

(2)

wherein $Ar_1$ to $Ar_6$ each represent an unsubstituted phenyl radical or a substituted phenyl radical having one or more substituents on the phenyl nucleus in which the substituents may be the same or different and each comprise an alkyl group of 1 to 4 carbon atoms, an alkoxy group of 1 to 4 carbon atoms, an amino group, an alkylamino group of 1 to 4 carbon atoms, a dialkylamino group of 1 to 4 carbon atoms, an alkylthio group of 1 to 4 carbon atoms, a halogen atom, or a halogenoalkyl group of 1 to 4 carbon atoms, and $R_1$ to $R_6$ may be the same or different and each represent a hydrogen atom or a methyl group, said process comprising the steps of converting at least one halogen compound of the general formula (1)

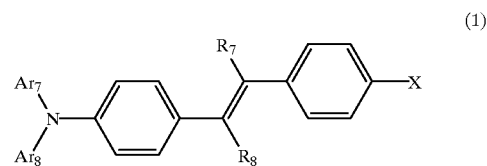

(1)

wherein $R_7$ and $R_8$ may be the same or different and each represent a hydrogen atom or a methyl group, $Ar_7$ and $Ar_8$ may be the same or different and each represent an unsubstituted phenyl radical or a substituted phenyl radical having one or more substituents on the phenyl nucleus in which the substituents may be the same or different and each comprise an alkyl group of 1 to 4 carbon atoms, an alkoxy group of 1 to 4 carbon atoms, an amino group, an alkylamino group of 1 to 4 carbon atoms, a dialkylamino group of 1 to 4 carbon atoms, an alkylthio group of 1 to 4 carbon atoms, a halogen atom, or a halogenoalkyl group of 1 to 4 carbon atoms, and X represents a halogen atom, into a lithio compound, and reacting the lithio compound with a nitrogen trihalide in which the three halogen atoms joined to the nitrogen atom may be the same or different.

2. A process for the preparation of a triphenylamine compound as claimed in claim 1 wherein the nitrogen trihalide is nitrogen trichloride ($NCl_3$), nitrogen trifluoride ($NF_3$) or nitrogen tribromide ($NBr_3$).

3. A process for the preparation of a triphenylamine compound as claimed in claim 1 wherein the substituent X in the compound of the general formula (1) is a chlorine atom, a bromine atom or an iodine atom.

4. A process for the preparation of a triphenylamine compound as claimed in claim 1 wherein the compound of the general formula (1) is 4-chloro-4'-(N,N-ditolylamino) stilbene and the compound of the general formula (2) is 4,4',4"-tris[4-(N,N-ditolylamino)styryl]triphenylamine.

5. A process for the preparation of a triphenylamine compound as claimed in claim 4 wherein the 4-chloro-4'-(N,N-ditolylamino)stilbene is obtained by reacting 4-chlorobenzyl chloride with triethyl phosphite to form a phosphorous ester, and reacting the phosphorous ester with 4-(4',4"-dimethyldiphenylamino)benzaldehyde.

6. A process for the preparation of a triphenylamine compound as claimed in claim 5 wherein the conversion of 4-chlorobenzyl chloride into a phosphorous ester is carried out by heating a mixture of 4-chlorobenzyl chloride and triethyl phosphite under reflux.

7. A process for the preparation of a triphenylamine compound as claimed in claim 4 wherein the conversion into a lithio compound is carried out with the aid of methyllithium or butyllithium.

8. A process for the preparation of a triphenylamine compound as claimed in claim 4 wherein the reaction with the nitrogen trihalide is carried out at a temperature of −20 to 0° C. in the presence of a solvent.

* * * * *